United States Patent
Lin et al.

(10) Patent No.: US 12,414,736 B2
(45) Date of Patent: Sep. 16, 2025

(54) OPTICAL MEASUREMENT SYSTEM

(71) Applicant: Advanced ACEBIOTEK CO., LTD., Hsinchu County (TW)

(72) Inventors: Yi-Ping Lin, Tainan (TW); Jyh-Chern Chen, New Taipei (TW); Shen-Fu Hsu, Hsinchu County (TW)

(73) Assignee: Advanced ACEBIOTEK CO., LTD., Hsinchu County (TW)

( * ) Notice: Subject to any disclaimer, the term of this patent is extended or adjusted under 35 U.S.C. 154(b) by 785 days.

(21) Appl. No.: 17/720,268

(22) Filed: Apr. 13, 2022

(65) Prior Publication Data
US 2023/0059771 A1 Feb. 23, 2023

(30) Foreign Application Priority Data
Aug. 17, 2021 (TW) ................. 110130197

(51) Int. Cl.
*G01N 21/39* (2006.01)
*A61B 5/00* (2006.01)
*A61B 5/1455* (2006.01)

(52) U.S. Cl.
CPC .......... *A61B 5/4331* (2013.01); *A61B 5/1455* (2013.01); *G01N 21/39* (2013.01); *G01N 2021/399* (2013.01)

(58) Field of Classification Search
CPC .............. A61B 5/1455; A61B 5/14551; A61B 5/14552
See application file for complete search history.

(56) References Cited

U.S. PATENT DOCUMENTS

| | | | |
|---|---|---|---|
| 4,223,680 A * | 9/1980 | Jobsis | A61B 5/14552 600/324 |
| 5,106,387 A | 4/1992 | Kittrell | |
| 5,701,902 A * | 12/1997 | Vari | A61B 5/0059 600/476 |
| 2003/0139667 A1* | 7/2003 | Hewko | A61B 5/0059 600/410 |
| 2009/0303475 A1 | 12/2009 | Jayaraman | |
| 2017/0303837 A1* | 10/2017 | Bechtel | A61B 5/14552 |

FOREIGN PATENT DOCUMENTS

| | | |
|---|---|---|
| CN | 1578905 A | 2/2005 |
| CN | 105928890 A | 9/2016 |
| TW | 200540416 | 12/2005 |

* cited by examiner

*Primary Examiner* — Eric F Winakur
(74) *Attorney, Agent, or Firm* — Winston Hsu

(57) ABSTRACT

An optical measurement system is provided, which includes a light source device, a fiber module, an optical detection device and a processing circuit. The light source device is configured to generate light to illuminate a target tissue area and a reference tissue area of a human body. The fiber module is configured to direct and transmit the light to illuminate the target tissue area and the reference tissue area and receive response beams from the target tissue area and the reference tissue area. The optical detection device is configured to detect the response beams from the target tissue area to obtain the target spectrum signal and detect the response beams from the reference tissue area to obtain a reference spectrum signal. The processing circuit configured to calculate a health status parameter of the target tissue area according to the target spectrum signal and reference spectrum signal.

13 Claims, 8 Drawing Sheets

OPTICAL MEASUREMENT SYSTEM

BACKGROUND OF THE INVENTION

1. Field of the Invention

The present invention relates to an optical measurement system, and more particularly, to an optical measurement system capable of providing health parameters of a target tissue area calculated by utilizing spectrum signals in real time.

2. Description of the Prior Art

A mucous membrane tissue, also called mucosal tissue, is apart of surface tissues of various organs of a human body exposed to the outside world. The mucosal tissue is a membranous structure composed of epithelial tissues and connective tissues. The mucosal tissue is an important part of the human body to contact with various antigens in nature. The mucosal tissue is not only associated with functions of organs, but also as the first line of defense of a human immune system. Conventional test methods for testing whether mucosal tissues are healthy, inflamed, cancerous, abnormal cell proliferation, or tumors may include computed tomography scan, nuclear magnetic resonance (NMR), ultrasonic tomography, optical coherence tomography, X-ray, endoscopy and pathology. Endoscopy is a common early diagnosis method for detecting serious diseases, but still has the limitations of poor image resolution, requirements of anesthesia or local gas inflation of organ cavity. Moreover, the endoscopy technique requires the assistance of contrast agent and thus is not suitable for patients having side effects from the contrast agent. Further, an optical biopsy method has gradually attracted attention in the field of biomedicine. The optical biopsy method may be applied and has the advantages of not requiring the collection of human tissue specimens and real time imaging for assisting medical diagnosis. However, the determination result of the conventional optical biopsy diagnosis method is still based on the image information of the mucosal surface. As such, the clinical professional may be prone to make erroneous judgments or have different opinions while making the medical diagnosis based on the image information. Thus, there is a need for improvement.

SUMMARY OF THE INVENTION

It is therefore a primary objective of the present invention to provide an optical measurement system capable of providing health parameters of target tissue area calculated by utilizing spectrum signals in real time.

According to an embodiment of the present invention, an optical measurement system is disclosed. The optical measurement system comprises a light source device configured to generate light to illuminate a target tissue area and a reference tissue area of a human body; a fiber module coupled to the light source device, and configured to direct and transmit the light generated by the light source device to illuminate the target tissue area and the reference tissue area of the human body, and receive response beams from the target tissue area and the reference tissue area of the human body; an optical detection device coupled to the fiber module, and configured to detect the response beams from the target tissue area to obtain a target spectrum signal of the target tissue area and detect the response beams from the reference tissue area to obtain a reference spectrum signal of the reference tissue area; and a processing circuit coupled to the light source device and optical detection device, and configured to calculate a health status parameter of the target tissue area according to the target spectrum signal and the reference spectrum signal.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the description and following claims to refer to particular components. As one skilled in the art will appreciate, hardware manufacturers may refer to a component by different names. This document does not intend to distinguish between components that differ in name but not function. In the following description and in the claims, the terms "include" and "comprise" are utilized in an open-ended fashion, and thus should be interpreted to mean "include, but not limited to . . . ". Also, the term "couple" is intended to mean either an indirect or direct electrical connection. Accordingly, if one device is coupled to another device, that connection may be through a direct electrical connection, or through an indirect electrical connection via other devices and connections.

Figure 1:
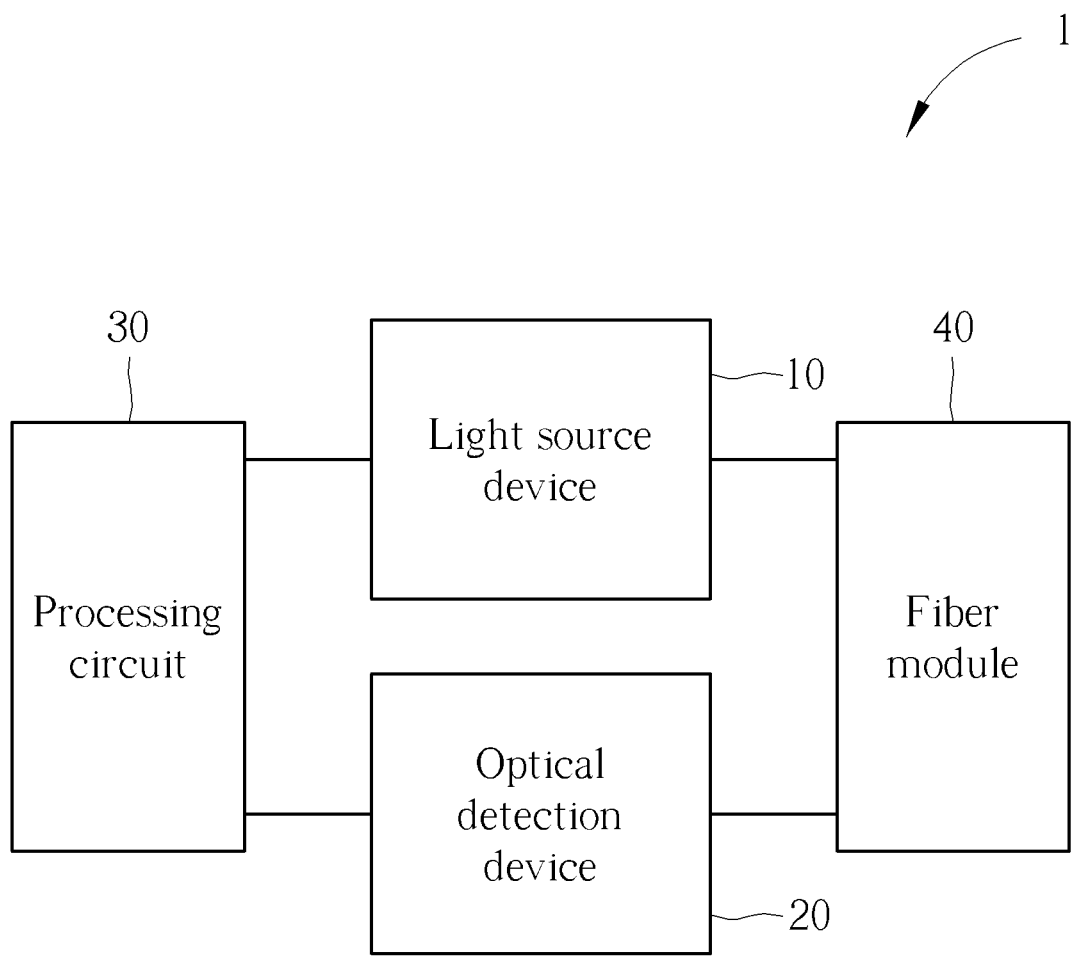
FIG. 1 is a schematic diagram of an optical measurement system according to an embodiment of the present invention.

Please refer to FIG. 1, which is a schematic diagram of an optical measurement system 1 according to an embodiment of the present invention. The optical measurement system 1 includes a light source device 10, an optical detection device 20, a processing circuit 30 and a fiber module 40. The light source device 10 is configured to generate light. The optical detection device 20 is configured to detect spectrum signals. The fiber module 40 is coupled to the light source device 10 and the optical detection device 20. The fiber module 40 is configured to direct and transmit the light generated by the light source device 10 to illuminate an area to be measured of a human body. Moreover, the fiber module 40 is configured to receive response beams (or called reaction beams) from the area to be measured of the human body and transmit the received response beams to the optical detection device 20. For example, the light source device 10 generates light. The light generated by the light source device 10 may be guided and transmitted to illuminate a target tissue area of the human body by the fiber module 40. The fiber module 40 receives response beams from the target tissue area to be measured and transmits the received response beams to the optical detection device 20. The optical detection device 20 detects the response beams from the target tissue area to obtain a target spectrum signal of the target tissue area. For example, the light source device 10 generates light and the fiber module 40 guides and transmits the light to illuminate a reference tissue area of the human body. The fiber module 40 receives response beams from the reference tissue area to be measured and transmits the received response beams to the optical detection device 20. The optical detection device 20 detects the response beams from the reference tissue area to obtain a reference spectrum signal of the reference tissue area. The processing circuit 30 is configured to calculate a health status parameter of the target tissue area according to the target spectrum signal and the reference spectrum signal. The light source device 10 may include infrared light emitting diodes, laser diodes or any other devices which can emit light. The processing circuit 30 may control the light source device 10 to generate the required light source. The optical detection device 20 may be an optical spectrum analyzer or a spectrometer, but not limited thereto.

The processing circuit 30 may calculate health status parameters of the target tissue area according to at least one of the target spectrum signal and the reference spectrum signal. The health status parameter includes at least one of a tissue oxygenation, a tissue inflammation, a tissue proliferation, a tissue uniformity, but not limited thereto. The processing circuit 30 may determine the health status of the target tissue area of the human body according to at least one of the health status parameters. The processing circuit 30 may be a central processing unit (CPU), a microprocessor, a digital signal processor (DSP), a programmable controller, a graphic processing unit (GPU) a programmable logic device (PLD), or other similar devices, or combination thereof, but not limited thereto.

Figure 2:
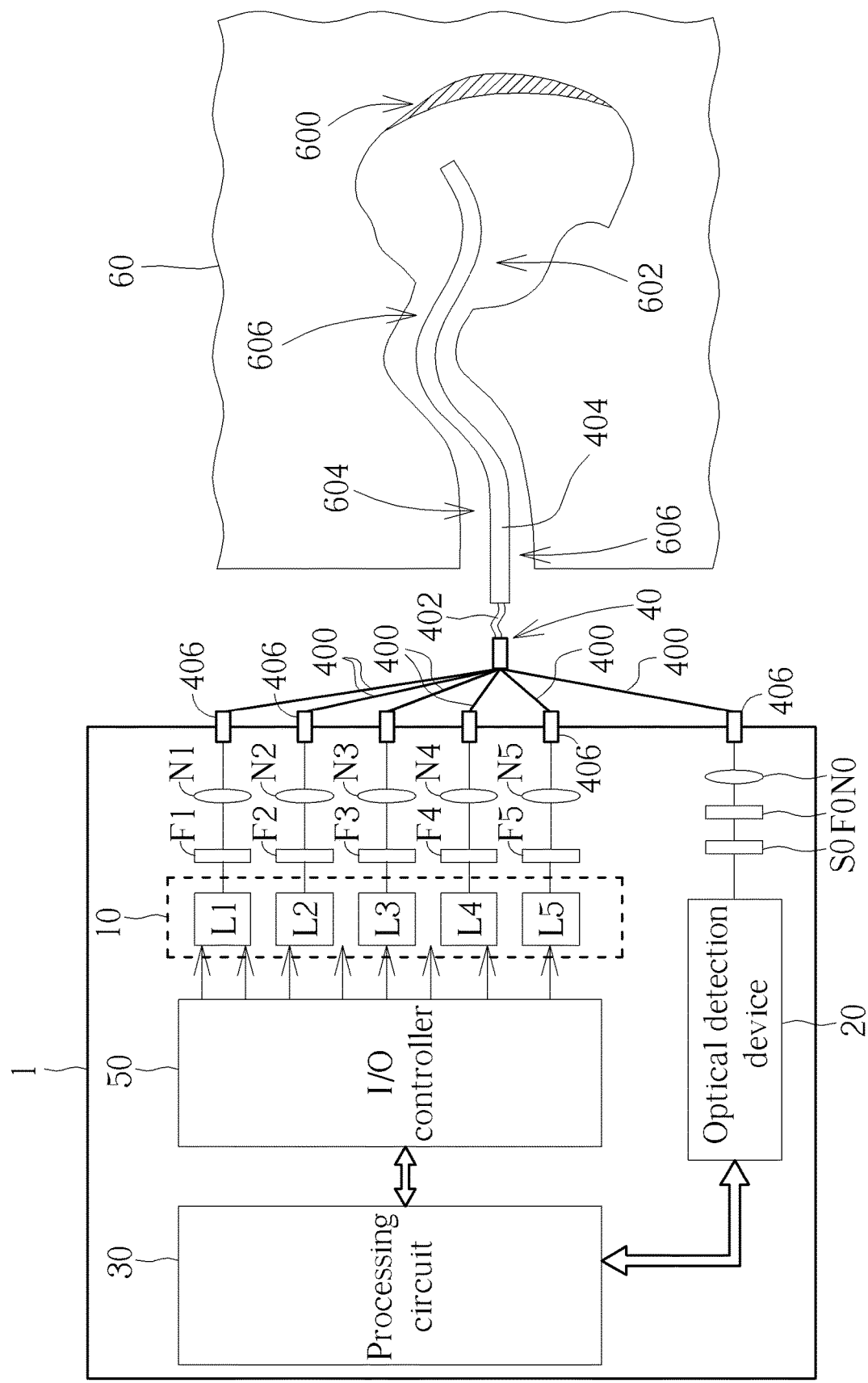
FIG. 2 is a schematic diagram of an optical measurement system according to an alternative embodiment of the present invention.

FIG. 2 is a schematic diagram of an optical measurement system 1 according to an alternative embodiment of the present invention. As shown in FIG. 2, the optical measurement system 1 further includes an input/output controller (I/O controller) 50, filters F0 to F5, lenses N0 to N5, and a slit 50. The light source device 10 includes light sources L1 to L5. The light source may be a single frequency light source or a broadband light source. For example, the light sources L1 and L2 may be broadband light sources, the light sources L3 to L5 may be single frequency light sources, but not limited thereto. As shown in FIG. 2, the light emitted by the light sources L1 to L5 may be passed through filter F1 to F5 and lenses N0 to N5 to enter the fiber module 40, respectively. For example, when one of the light sources L1 to L5 emits the light, the emitted light may be passed through a respective filter and a respective lens to enter the fiber module 40 and the fiber module 40 may direct the light to illuminate an area to be measured. Moreover, the fiber module 40 may also receive light, and the received light may be passed through the lens N0, the filter F0 and the slit 50 to enter the optical detection device 20.

The type, frequency and amount of light source of the light source device 10 may be varied and designed in accordance with different requirements. Each light source may include a light emitting diode (LED), a laser diode or any device which can emit light. For example, the light source may include single frequency light source with the wavelength of 280 nm, 365 nm, 405 nm, 522 nm, 465 nm, 532 nm, 600 nm, 637 nm, 750 nm, 785 nm, 800 nm or 1064 nm, but not limited thereto. For example, the light source may be a low-energy laser diode, such as a laser diode less than 80 mW. For example, the light source may include a broadband light source with a wavelength range of 200 nm to 500 nm, 400 nm to 600 nm, 500 nm to 650 nm, 400 nm to 900 nm, or 600 nm to 1050 nm. For example, the light source may be an LED, a xenon lamp, a deuterium lamp or a bromine tungsten lamp, but not limited thereto. For example, the filter F0 may be a notch filter or an edge filter, but not limited thereto. For example, the filters F1 to F5 may be laser line filters, but not limited thereto.

In an embodiment, the processing circuit 30 may control the light source device 10 to generate light. For example, as shown in FIG. 2, the input/output controller 50 is coupled between the processing circuit 30 and the light source device 10, and the processing circuit 30 may control the light source device 10 to generate light via the input/output controller 50. In the optical measurement system 1, the light emitted by the light source device 10 may be directed and transmitted to an area to be measured by the fiber module 40. The response beams from the area to be measured may be received and transmitted to the optical detection device 20 by the fiber module 40, such that the optical detection device 20 may detect and collect response beams of the area to be measured to generate the corresponding spectrum signals. The fiber module 40 includes a fiber bundle assembly 402, a fiber bundle assembly jacket 404 and a plurality of fiber connectors 406. The fiber bundle assembly 402 includes a plurality of fibers 400. The fibers 400 are coupled to the light source device 10 and the optical detection device 20 via the fiber connectors 406. The fiber bundle assembly jacket 404 is utilized for covering or surrounding the fiber bundle assembly 402 to protect the fiber bundle assembly 402. The fiber bundle assembly jacket 404 may be disposed and covered on the outer circumference of the fiber bundle assembly 402 after sterilization. The fiber bundle assembly 402 may be a disposable fiber bundle assembly that may be used only once. The fiber bundle assembly jacket 404 may be a disposable fiber bundle assembly jacket that may be used only once. The fiber bundle assembly jacket 404 may be made of a soft flexible material. The fiber bundle assembly jacket 404 may be made of a transparent material. The fiber bundle assembly jacket 404 may be made of the material selected from Teflon, silicon, polyethylene, polyurethane or polyvinyl chloride, but not limited thereto. Please further refer to FIG. 2. The fiber module 40 includes at least one fiber for directing the light emitted by the light source device 10 to illuminate the area to be measured, such as, the target tissue area or the reference tissue area. For example, as shown in FIG. 2, each of the lenses N1 to N5 is connected to a respective fiber connector 406 and fiber 400, and the light emitted by the light source device 10 may be directed to the area to be measured by the respective fiber 400. In an embodiment, the fiber module 40 include at least one fiber for receiving and transmitting the response beams of the area to be measured to the optical detection device 20, such that the optical detection device 20 may detect the corresponding spectrum signals. For example, as shown in FIG. 2, the lens N0 is connected to a respective fiber connector 406 and fiber 400. When the fiber module 40 receives the response beams from the area to be measured, the response beams from the area to be measured may be transmitted to the optical detection device 20 through the fiber connector 406, the fiber 400, the lens N0, the filter F0 and the slit 50.

The target tissue area and the reference tissue area of the embodiments may be living tissue areas of an organism. For example, the target tissue area and the reference tissue area of the embodiments may be living tissue areas of the same human body. The reference tissue area of the embodiments may be healthy tissues of the same human body as the target tissue area. The target tissue area and the reference tissue area of the embodiments may be tissue areas of the same human body, and the reference tissue area may be healthy tissues of the same human body. The target tissue area and the reference tissue area of the embodiments may be mucosal tissues of the human body or animal or other biological tissues. For example, the target tissue area may be a mucosal tissue of a human body, but not limited thereto. For example, the reference tissue area may be the healthy tissue of a pad of a healthy finger or an inner side of a healthy thigh, but not limited thereto. The mucosal tissue may include mucosa of conjunctiva of eye, oral mucosa, nasopharyngeal mucosa, respiratory mucosa, lung mucosa, esophageal mucosa, gastric mucosa, intestinal mucosa, urethral mucosa, genital mucosa, urinary tract, genital mucosa and uterine mucosa (or called endometrium), but not limited thereto.

For example, when the target tissue area and the reference tissue area to be measured are a mucosal tissue 600 of a human body 60, the fiber module 40 may be inserted into a canal 604 through an opening 606 of the human body 60 and entered into a cavity 602 of the human body 60. Since the fiber bundle assembly jacket 404 has been sterilized, the human to be measured may not be infected. As shown in FIG. 2, the light generated by the light source device 10 may be guided to illuminate the mucosal tissue 600 of the human body 60. As such, specific biochemical molecules in the mucosal tissue 600 may be excited by the light emitted by the light source device 10 so as to produce response beams generated by reflection, Raman scattering, fluorescence or phosphorescence reactions. The response beams may include reflected light and/or scattered light. The mucosal tissue may include a plurality of biomarker molecules with spontaneous fluorescence property, such as, NADP, NADPH, NADH, FAD, [CP(OME)3], [CP(ME)3], collagen, hemoglobin, porphyrin, porphyrin derivative. The response beams may be received and guided to the optical detection device 20 through the fiber 400 of the fiber module 40, such that the optical detection device 20 may detect and analyze the response beams to obtain the corresponding spectrum signals. The spectrum signals detected by the optical detection device 20 may reflect the type and concentration of biomolecules in mucosal tissue or mucosal tissue fluid. The processing circuit 30 may determine the oxygen content in the mucosal tissue, proliferation of cells, inflammation, thickness and uniformity of the mucosal tissue based on the spectrum signals detected by the optical detection device 20. Therefore, the embodiments of the present invention may provide the health status parameters of the real-time spectral signals for the following determination of health status, thus realizing an instantaneous and accurate measurement. Compared with the conventional endoscope method, the optical inspection system 1 of the embodiments of the present invention may significantly reduce the discomfort and pain for the person to be measured during the measurement process. Furthermore, the conventional optical laser diagnosis method is typically performed based on the image information of the mucosal surface for diagnosis. In comparison, the detection result of the embodiments of the present invention may be quantifiable values rather than the images that cannot be quantified, thus reducing the probability of human errors caused by naked eye judgment. The embodiments of the present invention may also provide real-time health parameters which are calculated and determined by utilizing spectrum signals and accurately utilized as reference values for early mucosal symptoms, thus significantly improving diagnostic accuracy.

Figure 3:
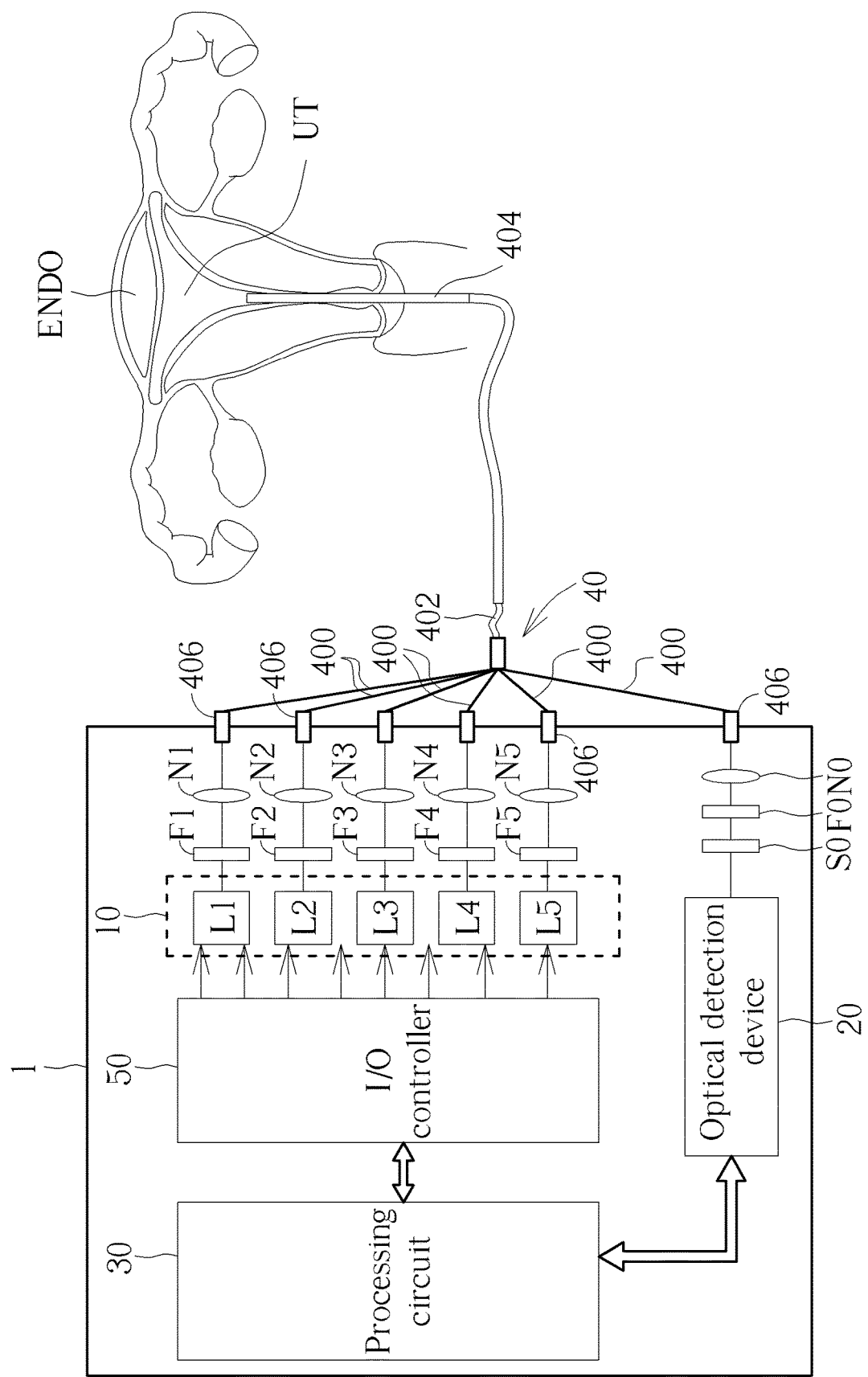
FIG. 3 is a schematic diagram of an optical measurement system applied to endometrial measurement according to an embodiment of the present invention.

FIG. 3 is a schematic diagram of an optical measurement system 1 applied to endometrial measurement according to an embodiment of the present invention. For example, the optical measurement system 1 may be applied in an endometrial measurement device. The target tissue area to be measured may be a mucosal tissue of endometrium of a human body. For example, the target tissue area to be measured may be the endometrium located at the fundus of the uterus, the cavity of uterine, the entrance of uterus adjacent to a cervix, the internal of a cervix, or the external of a cervix, but not limited thereto. As shown in FIG. 3, the fiber module 40 may be inserted into a cavity of a uterus UT, such that the light generated by the light source device 10 may be guided to illuminate an endometrium ENDO via the fiber module 40. Specific biochemical molecules in the endometrium ENDO may be excited by the light emitted by the light source device 10 so as to produce response beams generated by reflection, Raman scattering, fluorescence or phosphorescence reactions. The response beams may be received and guided to the optical detection device 20 through the fiber 400 of the fiber module 40, such that the optical detection device 20 may detect and analyze the response beams to obtain the corresponding spectrum signals.

Further description associated with the operations of optical measurement system 1 is provided as follows. In an embodiment, the health status parameter includes a tissue oxygenation. The light source device 10 is configured to generate broadband light having a wavelength range $W_R$ between 300 nm and 380 nm, 400 nm and 600 nm, 500 nm and 650 nm, 600 nm and 850 nm, 650 nm and 950 nm or 400 nm and 900 nm, but not limited thereto. For example, the target tissue area to be measured is a mucosal tissue (e.g., endometrium) of a human body. The reference tissue area is a healthy tissue of the same human body as the target tissue area. For example, the reference tissue area may be a healthy pad of a thumb of the human body. The light source device 10 is configured to generate broadband light with the wavelength range $W_R$ to illuminate the reference tissue area (e.g., pad of thumb). The optical detection device 20 is configured to detect response beams from the reference tissue area to obtain a reference spectrum signal $S_R$ of the reference tissue area (e.g., pad of thumb). For example, the optical detection device 20 may detect and collect response beams reflected or scattered by the reference tissue area or produced by the fluorescence reaction or phosphorescence reaction of the reference tissue area to generate the reference spectrum signal $S_R$. Moreover, the light source device 10 is configured to generate the broadband light with the wavelength range $W_R$ to illuminate the target tissue area (e.g., endometrium). The optical detection device 20 may detect a target spectrum signal $S_T$ from the target tissue area. For example, the optical detection device 20 may detect and collect response beams reflected or scattered by the target tissue area or produced by the fluorescence reaction or phosphorescence reaction of the target tissue area to generate the target spectrum signal $S_T$.

Moreover, the processing circuit 30 is configured to calculate the tissue oxygenation corresponding to the target tissue area according to the target spectrum signal $S_T$ and the reference spectrum signal $S_R$. The processing circuit 30 may determine a reference intensity value of the reference spectrum signal $S_R$ at a first characteristic wavelength since the reference spectrum signal $S_R$ is detected by the optical detection device 20. For example, the first characteristic wavelength may be 520 nm, 530 nm, 540 nm, 568 nm, 578 nm, 588 nm, 595 nm, 608 nm, 650 nm, 660 nm, 670 nm or 800 nm, but not limited thereto. For example, the first characteristic wavelength may be associated with a characteristic wavelength of oxygenated hemoglobin. For example, the first characteristic wavelength may be between 568 nm and 588 nm or between 650 nm and 670 nm. For example, the first characteristic wavelength may be within the wavelength range $W_R$. The processing circuit may analyze and determine at least one reference peak intensity value of the reference spectrum signal $S_R$ in a first wavelength range. Each reference peak intensity value corresponds to a respective wavelength in the first wavelength range. Each reference peak intensity value may be greater than the reference intensity value of the reference spectrum signal $S_R$ at the first characteristic wavelength. The processing circuit 30 may calculate a reference absorption intensity value of the reference spectrum signal $S_R$ at the first characteristic wavelength according to the at least one reference peak intensity value of the reference spectrum signal $S_R$ in the first wavelength range and the reference intensity value of the reference spectrum signal $S_R$ at the first characteristic wavelength. For example, the processing circuit 30 may calculate an average value of the at least one reference peak intensity value of the reference spectrum signal $S_R$ in the first wavelength range and calculate the reference absorption intensity value of the reference spectrum signal $S_R$ at the first characteristic wavelength by subtracting the reference intensity value of the reference spectrum signal $S_R$ at the first characteristic wavelength from the average value of the at least one reference peak intensity value.

The processing circuit 30 may determine a target intensity value of the target spectrum signal $S_T$ detected by the optical detection device 20 at the first characteristic wavelength. The processing circuit may analyze and determine at least one target peak intensity value of the target spectrum signal $S_T$ in the first wavelength range. Each target peak intensity value corresponds to a respective wavelength in the first wavelength range. Each target peak intensity value may be greater than the target intensity value of the target spectrum signal $S_T$ at the first characteristic wavelength. The processing circuit 30 may calculate a target absorption intensity value of the target spectrum signal $S_T$ at the first characteristic wavelength according to the at least one target peak intensity value of the target spectrum signal $S_T$ in the first wavelength range and the target intensity value of the target spectrum signal $S_T$ at the first characteristic wavelength. For example, the processing circuit 30 may calculate an average value of the at least one target peak intensity value of the target spectrum signal $S_T$ in the first wavelength range and calculate the target absorption intensity value of the target spectrum signal $S_T$ at the first characteristic wavelength by subtracting the target intensity value of the target signal $S_T$ at the first characteristic wavelength from the average value of the at least one target peak intensity value. Further, the processing circuit 30 may calculate the tissue oxygenation of the target tissue area by dividing the target absorption intensity value of the target spectrum signal $S_T$ at the first characteristic wavelength by the reference absorption intensity value of the reference spectrum signal $S_R$ at the first characteristic wavelength. Therefore, the processing circuit 30 may evaluate and determine the health status of the target tissue area according to the tissue oxygenation of the target tissue area.

Figure 4:
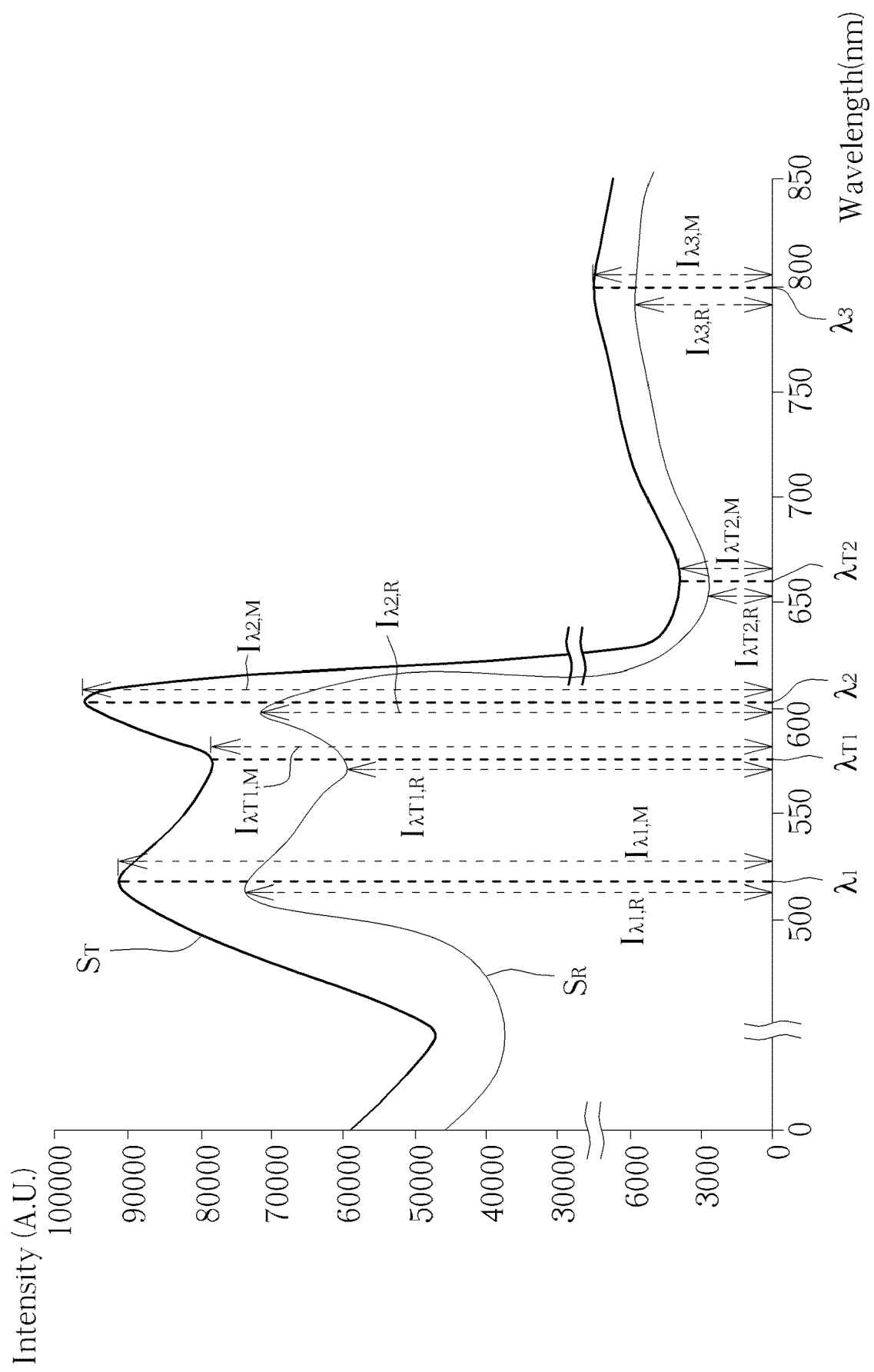
FIG. 4 to FIG. 8 are schematic diagrams illustrating the spectrum signals detected by the optical detection device according to alternative embodiments of the present invention.

Please refer to FIG. 4, which is a schematic diagram illustrating the spectrum signals detected by the optical detection device 20 according to a first embodiment of the present invention. For example, the wavelength range $W_{R1}$ is between 500 nm and 650 nm. The characteristic wavelength $\lambda_{T1}$ is 578 nm. The characteristic wavelength $\lambda_{T1}$ is associated with a characteristic wavelength of oxygenated hemoglobin. The light source device 10 is configured to generate broadband light with a wavelength range between 400 nm and 900 nm to illuminate the target tissue area (e.g., endometrium) and the optical detection device 20 is configured to detect a target spectrum signal $S_T$ from the target tissue area. The light source device 10 is configured to generate the broadband light with a wavelength range between 400 nm and 900 nm to illuminate the reference tissue area (e.g., pad of thumb), and the optical detection device 20 is configured to detect a reference spectrum signal $S_R$ from the reference tissue area. The processing circuit 30 may select an intensity value at which a turning point occurs in the reference spectrum signal $S_R$ within the wavelength range $W_{R1}$ for acting as a reference peak intensity value of the reference spectrum signal $S_R$. For example, a turning point occurs in the intensity curve of the reference spectrum signal $S_R$ when the intensity value of the reference spectrum signal $S_R$ changes from increasing to decreasing and thus the intensity value at the turning point of the reference spectrum signal $S_R$ may be selected as the reference peak intensity value. For example, as shown in FIG. 4, in the wavelength range $W_{R1}$, i.e., between 500 nm and 650 nm, a turning point occurs on the intensity curve of reference spectrum signal $S_R$ at the wavelength $\lambda_1$ (520 nm) and another turning point occurs on the intensity curve of reference spectrum signal $S_R$ at the wavelength $\lambda_2$ (608 nm). As such, the processing circuit 30 determines that the intensity value $I_{\lambda 1,R}$ corresponding to the wavelength $\lambda_1$ and the reference intensity value $I_{\lambda 2,R}$ corresponding to the wavelength $\lambda 2$ of the reference spectrum signal $S_R$ as the reference peak intensity values of the reference spectrum signal $S_R$ in the wavelength range $W_{R1}$. The reference intensity values $I_{\lambda 1,R}$ and $I_{\lambda 2,R}$ are greater than the reference intensity value $I_{\lambda T1,R}$ of the reference spectrum signal $S_R$ at the characteristic wavelength $\lambda_{T1}$. The processing circuit 30 may calculate a reference absorption intensity value $J_{\lambda T1,R}$ of the reference spectrum signal $S_R$ at the characteristic wavelength $\lambda_{T1}$ according to the reference peak intensity values $I_{\lambda 1,R}$ and $I_{\lambda 2,R}$ of the reference spectrum signal $S_R$ in the wavelength range $W_{R1}$ and the reference intensity value $I_{\lambda T1,R}$ of the reference spectrum signal $S_R$ at the characteristic wavelength $\lambda_{T1}$. The reference absorption intensity value $J_{\lambda T1,R}$ of the reference spectrum signal $S_R$ at the characteristic wavelength $\lambda_{T1}$ may be calculated by the processing circuit 30 according to the following equation:

$$J_{\lambda T1,R}(I_{\lambda 1,R}+I_{\lambda 2,R})/2 - I_{\lambda 1,R} \tag{1}$$

The processing circuit 30 may select a intensity value at which a turning point occurs in the target spectrum signal $S_T$ within the wavelength range $W_{R1}$ and greater than the target intensity value $I_{\lambda T1,M}$ of the target spectrum signal $S_T$ at the characteristic wavelength $\lambda_{T1}$ for acting as a target peak intensity value of the target spectrum signal $S_T$. As shown in FIG. 4, in the wavelength range $W_{R1}$, i.e., between 500 nm and 650 nm, a turning point occurs on the intensity curve of target spectrum signal $S_T$ at the wavelength $\lambda_1$ (520 nm) and another turning point occurs on the intensity curve of target spectrum signal $S_T$ at the wavelength $\lambda 2$ (608 nm). The processing circuit 30 determines that the intensity value $I_{\lambda 1,M}$ corresponding to the wavelength $\lambda_1$ and the intensity value $I_{\lambda 2,M}$ corresponding to the wavelength $\lambda 2$ of the target spectrum signal $S_T$ as the target peak intensity values of the target spectrum signal $S_T$ in the wavelength range $W_{R1}$. The target intensity values $I_{\lambda 1,M}$ and $I_{\lambda 2,M}$ are greater than the target intensity value $I_{\lambda T1,M}$ of the target spectrum signal $S_T$ at the characteristic wavelength $\lambda_{T1}$. The processing circuit 30 may calculate a target absorption intensity value $J_{\lambda 1,M}$ of the target spectrum signal $S_T$ at the characteristic wavelength $\lambda_{T1}$ according to the target peak intensity values $I_{\lambda 1,M}$ and $I_{\lambda 2,M}$ of the target spectrum signal $S_T$ in the wavelength range $W_{R1}$ and the target intensity value $I_{\lambda T1,M}$ of the target spectrum signal $S_T$ at the characteristic wavelength $\lambda_{T1}$. The target absorption intensity value $J_{\lambda T1,M}$ of the target spectrum signal $S_T$ at the characteristic wavelength $\lambda_{T1}$ may be calculated by the processing circuit 30 according to the following equation (2). The tissue oxygenation $O_1$ of the target tissue area at the characteristic wavelength $\lambda_{T1}$ may be calculated by the processing circuit 30 according to the following equation (3):

$$J_{\lambda T1,M} = (I_{\lambda 1,M} + I_{\lambda 2,M})/2 - I_{\lambda T1,M} \qquad (2)$$

$$O_1 = J_{\lambda T1,M}/J_{\lambda T1,M} \qquad (3)$$

As the tissue oxygenation of the target tissue area is calculated, the processing circuit 30 may evaluate and determine the health status of the target tissue area according to the tissue oxygenation of the target tissue area. In addition, the reference absorption intensity value of the reference spectrum signal $S_R$ at the characteristic wavelength $\lambda_{T1}$ and the target absorption intensity value of the target spectrum signal $S_T$ at the characteristic wavelength $\lambda_{T1}$ may be calculated by using other methods. After that, the processing circuit 30 may calculate the tissue oxygenation of the target tissue area by dividing the target absorption intensity value of the target spectrum signal $S_T$ at the first characteristic wavelength by the reference absorption intensity value of the reference spectrum signal $S_R$ at the first characteristic wavelength.

Please further refer to FIG. 4. For example, the wavelength range $W_{R2}$ is between 650 nm and 850 nm. The characteristic wavelength $\lambda_{T2}$ is 660 nm. The characteristic wavelength $\lambda_{T2}$ is associated with a characteristic wavelength of oxygenated hemoglobin. The light source device 10 is configured to generate broadband light with a wavelength range between 400 nm and 900 nm to illuminate the target tissue area (e.g., endometrium) and the reference tissue area (e.g., pad of thumb). The optical detection device 20 is configured to detect a target spectrum signal $S_T$ from the target tissue area and a reference spectrum signal $S_R$ from the reference tissue area. As shown in FIG. 4, in the wavelength range $W_{R2}$, i.e., between 650 nm and 850 nm, a turning point occurs on the intensity curve of reference spectrum signal $S_R$ at the wavelength $\lambda_3$ (800 nm). The reference intensity values $I_{\lambda 3,R}$ of the reference spectrum signal $S_R$ is greater than the reference intensity value $I_{\lambda T2,R}$ of the reference spectrum signal $S_R$ at the characteristic wavelength $\lambda_{T2}$. The processing circuit 30 determines that the intensity value $I_{\lambda 3,R}$ corresponding to the wavelength $\lambda_3$ of the reference spectrum signal $S_R$ as the reference peak intensity values of the reference spectrum signal $S_R$ in the wavelength range $W_{R2}$. There is no need to perform an average operation since only one reference peak intensity values of the reference spectrum signal $S_R$ in the wavelength range $W_{R2}$ is obtained. The processing circuit 30 may calculate a reference absorption intensity value $J_{\lambda T2,R}$ of the reference spectrum signal $S_R$ at the characteristic wavelength $\lambda_{T2}$ by subtracting the reference intensity value $I_{\lambda T2,R}$ of the reference signal $S_R$ at the characteristic wavelength $\lambda_{T2}$ from the intensity value $I_{\lambda 3,R}$ corresponding to the wavelength $\lambda_3$ of the reference spectrum signal $S_R$ (i.e. $J_{\lambda T2,R} = I_{\lambda 3,R} - I_{\lambda T2,R}$). As shown in FIG. 4, in the wavelength range $W_{R2}$, i.e., between 650 nm and 850 nm, a turning point occurs on the intensity curve of target spectrum signal $S_T$ at the wavelength $\lambda_3$ (800 nm). The target intensity values $I_{\lambda 3,M}$ of the target spectrum signal $S_T$ is greater than the target intensity value $I_{\lambda T2,M}$ of the target spectrum signal $S_T$ at the characteristic wavelength $\lambda_{T2}$. The processing circuit 30 determines that the intensity value $I_{\lambda 3,M}$ corresponding to the wavelength $\lambda_3$ of the target spectrum signal $S_T$ as the target peak intensity values of the target spectrum signal $S_T$ in the wavelength range $W_{R2}$. The processing circuit 30 may calculate a target absorption intensity value $J_{\lambda T2,M}$ of the target spectrum signal $S_T$ at the characteristic wavelength $\lambda_{T2}$ by subtracting the target intensity value $I_{\lambda T2,M}$ of the target spectrum signal $S_T$ at the characteristic wavelength $\lambda_{T2}$ from the intensity value $I_{\lambda 3,M}$ corresponding to the wavelength $\lambda_3$ of the target spectrum signal $S_R$ (i.e., $J_{\lambda T2,M} = I_{\lambda 3,M} - I_{\lambda T2,M}$). The processing circuit 30 may calculate the tissue oxygenation $O_2$ of the target tissue area at the characteristic wavelength $\lambda_{T2}$ by dividing the target absorption intensity value $J_{\lambda T2,M}$ of the target spectrum signal $S_T$ at the characteristic wavelength $\lambda_{T2}$ by the reference absorption intensity value $J_{\lambda T2,R}$ of the reference spectrum signal $S_R$ at the characteristic wavelength $\lambda_{T2}$ (i.e., $O_2 = J_{\lambda T2,M}/J_{\lambda T2,R}$). Therefore, the processing circuit 30 may evaluate and determine the health status of the target tissue area according to the tissue oxygenation $O_2$ of the target tissue area.

Cancer or inflammatory cells may often preserve the state of continuous replication, so that high energy consumption may be required to facilitate metabolic activities and the abnormal proliferation of capillaries may also occur. Different from normal cells, the cancer cells may have a strong content of abnormal metabolic molecules, leading to abnormal blood oxygenation, uneven mucosal structure and abnormal microbial flora due to hypoxia. Therefore, the processing circuit 30 may determine the health status of the target tissue area of the human body according to the tissue oxygenation of the target tissue area. For example, the health status of the endometrium is one of the major factors causing female infertility. The endometrium is receptive to the embryo only during a specific window of implantation (WOI) period, and every woman has her own personalized WOI period. The conventional pathological diagnosis methods for the endometrium usually adopt blood biochemical test, endoscopy, ultrasound scan, pathological examination of endometrial curettage specimen or endometrial receptivity analysis (ERA). However, since the result of the blood biochemical test is easy to be affected by the body constitution or the menstrual period, the result of the blood biochemical test may be used as a reference index and insufficient to determine whether the uterine structure is abnormal. Endoscopy and ultrasound scan may merely check the structure of the endometrium, but is insufficient to determine whether physiological function is normal. Endometrial scraping or curettage specimen is an invasive examination. The human to be tested needs local anesthesia which may cause pain or bleeding. In addition, the specimen must be sent to the pathology department to wait for pathomorphological examination. Moreover, the oxygen content of tissues may vary during the menstrual period. For example, the tissue oxygenation on the 13th day of the menstrual period may be different from the tissue oxygenation on the 18th day of the menstrual period. The tissue oxygenation may also increase, remain flat or decrease. The embodiments of the present invention may calculate the tissue oxygenation of the target tissue area according to the target spectrum signal corresponding to the target tissue area and the reference spectrum signal corresponding to the reference tissue area, and accordingly determine the WOI period, the degree of tissue hypoxia and the cause of hypoxia for monitoring the health condition of the mucosal tissues by examining and observing the changes in tissue oxygenation during menstruation period.

In an embodiment, the health status parameter includes a tissue proliferation. The light source device 10 is configured to generate single frequency light. For example, the wavelength of the single frequency light emitted by the light source device 10 may be 522 nm, 532 nm, 600 nm, 637 nm, 673 nm, 750 nm, 785 nm or 800 nm, but not limited thereto. For example, the target tissue area to be measured is a mucosal tissue (e.g., endometrium). The reference tissue area is a healthy tissue of the same human body as the target tissue area. For example, the reference tissue area may be a healthy pad of a thumb or an inner side of a healthy thigh of the human body. The light source device 10 is configured to generate the single frequency light to illuminate the reference tissue area. The optical detection device 20 is configured to detect the response beams from the reference tissue area to obtain a reference spectrum signal $S_R$ of the reference tissue area. The light source device 10 is configured to generate the single frequency light to illuminate the target tissue area. The optical detection device 20 is configured to detect the response beams from the target tissue area to obtain a target spectrum signal $S_T$ of the target tissue area. Moreover, the processing circuit 30 is configured to calculate the tissue proliferation corresponding to the target tissue area according to the reference spectrum signal $S_R$ and the target spectrum signal $S_T$. The processing circuit 30 may calculate a reference intensity integration area of the reference spectrum signal $S_R$ in a first wavelength range. The processing circuit 30 may sum up the intensity values of the reference spectrum signal $S_R$ in the first wavelength range to obtain the reference intensity integration area. The first wavelength range may be between 300 nm and 380 nm, 400 nm and 600 nm, 500 nm and 650 nm, 600 nm and 850 nm, 640 nm and 800 nm, 400 nm and 900 nm or 600 nm and 1050 nm, but not limited thereto. The processing circuit 30 may calculate a target intensity integration area of the target spectrum signal $S_T$ in the first wavelength range. The processing circuit 30 may sum up the intensity values of the target spectrum signal $S_T$ in the first wavelength range to obtain the target intensity integration area. The processing circuit 30 may calculate the tissue proliferation of the target tissue area by dividing target intensity integration area of the target spectrum signal $S_T$ in the first wavelength range by the reference intensity integration area of the reference spectrum signal $S_R$ in the first wavelength range. Therefore, the processing circuit 30 may evaluate and determine the health status of the target tissue area according to the tissue proliferation of the target tissue area.

Figure 5:
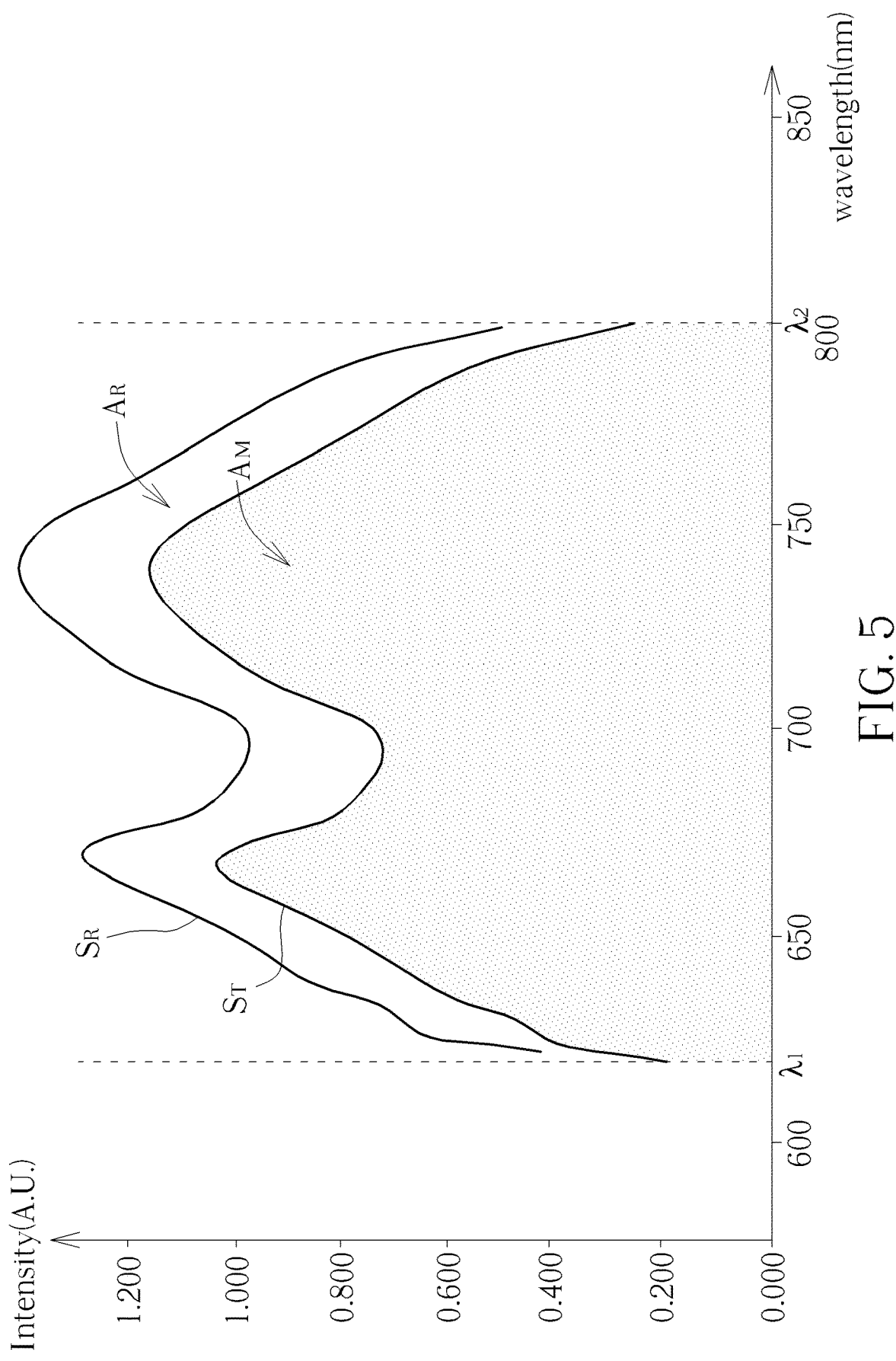

Please refer to FIG. 5, which is a schematic diagram illustrating the spectrum signals detected by the optical detection device 20 according to a second embodiment of the present invention. For example, the wavelength range $W_{R1}$ is between 640 nm and 800 nm. The light source device 10 is configured to generate single frequency light (e.g., the wavelength of the single frequency light is 600 nm) to illuminate the target tissue area (e.g., endometrium). The optical detection device 20 is configured to detect the response beams from the target tissue area to obtain a target spectrum signal $S_T$ of the target tissue area. The light source device 10 is configured to generate single frequency light (e.g., the wavelength of the single frequency light is 600 nm) to illuminate the reference tissue area (e.g., healthy pad of thumb or inner side of thigh). The optical detection device 20 is configured to detect the response beams from the reference tissue area to obtain a reference spectrum signal $S_R$ of the tissue area. As shown in FIG. 5, the processing circuit 30 may perform an intensity integration operation on the reference spectrum signal $S_R$ in the wavelength range $W_{R1}$ to obtain a reference intensity integration area $A_R$ of the reference spectrum signal $S_R$. The reference intensity integration area $A_R$ may be the area under the spectrum curve of the reference spectrum signal $S_R$ between 640 nm and 800 nm. The processing circuit 30 performs an intensity integration operation on the target spectrum signal $S_T$ in the wavelength range $W_{R1}$ to obtain a target intensity integration area $A_M$ of the target spectrum signal $S_T$. The target intensity integration area $A_M$ may be the area under the spectrum curve of the target spectrum signal $S_T$ between 640 nm and 800 nm. The processing circuit 30 may calculate the tissue proliferation of the target tissue area by dividing target intensity integration area $A_M$ of the target spectrum signal $S_T$ in the wavelength range $W_{R1}$ by the reference intensity integration area $A_R$ of the reference spectrum signal $S_R$ in the first wavelength range $W_{R1}$ (i.e., $A_M/A_R$). The tissue proliferation of tissues may vary during the menstrual period. For example, the tissue proliferation on the 13th day of the menstrual period may be different from the tissue proliferation on the 18th day of the menstrual period. The tissue proliferation may also increase, remain flat or decrease. The embodiments of the present invention may calculate the tissue proliferation of the target tissue area according to the target spectrum signal corresponding to the target tissue area and the reference spectrum signal corresponding to the reference tissue area. For example, as the tissue proliferation of the target tissue area does not fall within the normal range of healthy mucosal tissue, this means there is insufficient proliferative capacity of endometrial cell to pregnancy, and thus the person to be measured is hard to get pregnant at this time and is currently not in the period of window of implantation.

In an embodiment, the health status parameter includes a tissue inflammation. The light source device 10 is configured to generate single frequency light. For example, the wavelength of the single frequency light emitted by the light source device 10 may be 522 nm, 532 nm, 600 nm, 637 nm, 673 nm, 750 nm, 785 nm or 800 nm, but not limited thereto. For example, the target tissue area to be measured is a mucosal tissue (e.g., endometrium). The light source device 10 is configured to generate the single frequency light to illuminate the target tissue area. The optical detection device 20 is configured to detect the response beams from the target tissue area to obtain a target spectrum signal $S_T$ of the target tissue area. Moreover, the processing circuit 30 is configured to calculate the tissue inflammation corresponding to the target tissue area according to the target spectrum signal $S_T$. The processing circuit 30 is configured to determine a first intensity value of the target spectrum signal $S_T$ at a first wavelength of a first wavelength range and determine a second intensity value of the target spectrum signal $S_T$ at a second wavelength of a second wavelength range since the target spectrum signal $S_T$ is detected by the optical detection device 20. In an embodiment, the first wavelength range is different from the second wavelength range. The first wavelength range is associated with a characteristic spectrum range of porphyrin or porphyrin derivative. The porphyrin derivative may include protoporphyrin IX, Octaethylporphyrin, tetraphenylporphyrin, benzoporphyrin, porphobilinogen, uroporphyrinogen III or coproporphyrin, but not limited thereto. The first wavelength range may be a characteristic spectrum range in which the porphyrin exhibits strong reflected light intensity. The processing circuit 30 is configured to calculate the tissue inflammation corresponding to the target tissue area by dividing the first intensity value of the target spectrum signal $S_T$ at the first wavelength by the second intensity value of the target spectrum signal $S_T$ at the second wavelength. The tissue inflammation corresponding to the target tissue area may be utilized for measuring and estimating microorganisms in the endometrium, metabolite molecules produced by the microorganisms in the endometrium or inflammatory molecules produced by microorganisms in the endometrium. Therefore, the processing circuit 30 may determine the health status of the target tissue area according to the tissue inflammation corresponding to the target tissue area.

Figure 6:
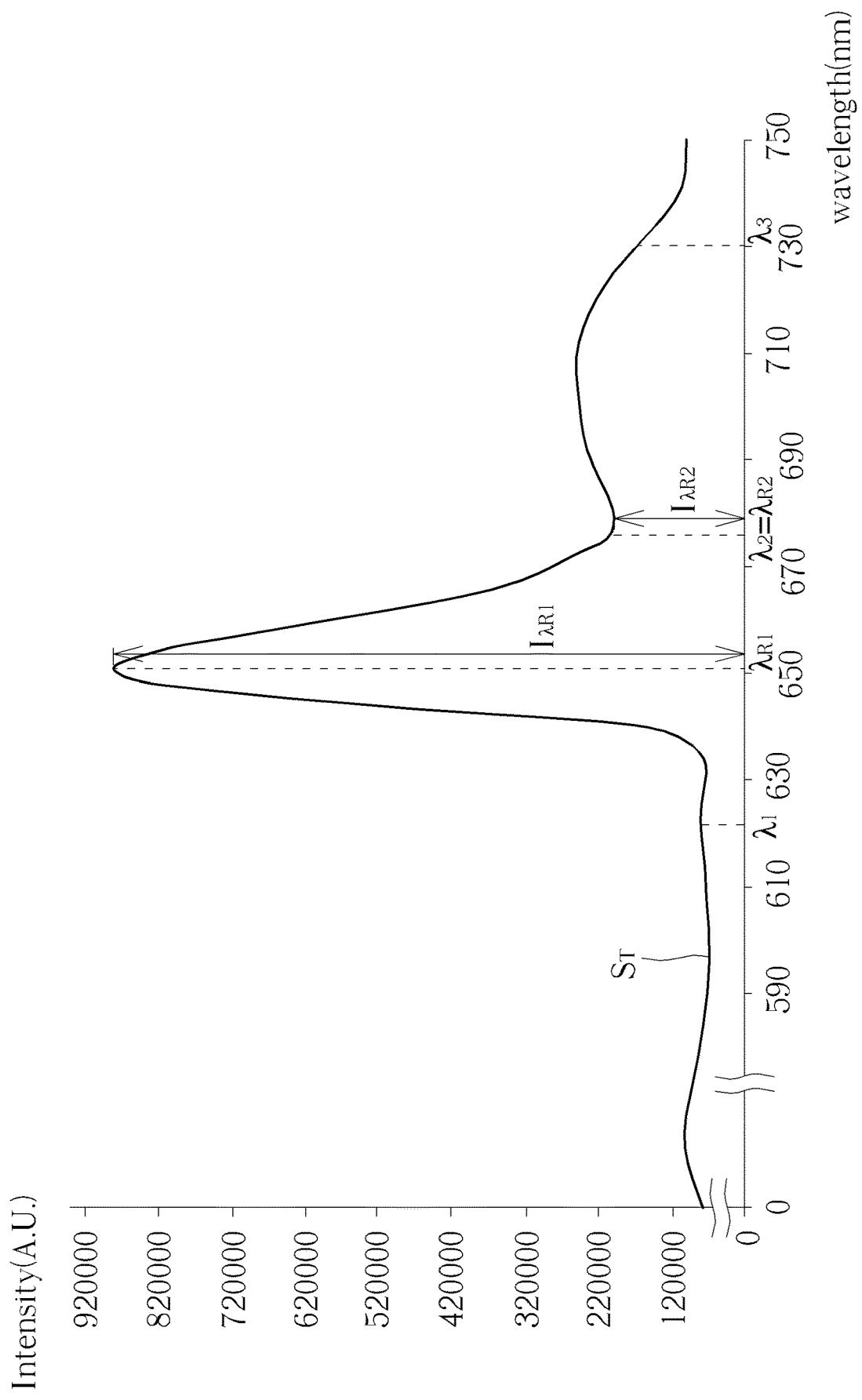

Please refer to FIG. 6, which is a schematic diagram illustrating the spectrum signals detected by the optical detection device 20 according to a third embodiment of the present invention. The wavelength range $W_{R1}$ is between a wavelength $\lambda_1$ and a wavelength $\lambda_2$. For example, the wavelength $\lambda_1$ is 620 nm, the wavelength $\lambda_2$ is 675 nm and the wavelength range $W_{R1}$ is between 620 nm and 675 nm. The wavelength range $W_{R2}$ is between the wavelength $\lambda_2$ and a wavelength $\lambda_3$. For example, the wavelength $\lambda_2$ is 675 nm, the wavelength $\lambda_3$ is 730 nm and the wavelength range $W_{R2}$ is between 675 nm and 730 nm. The light source device 10 is configured to generate single frequency light to illuminate the target tissue area (e.g., endometrium) and the optical detection device 20 is configured to detect a target spectrum signal $S_T$ from the target tissue area. As shown in FIG. 6, the processing circuit 30 is configured to determine an intensity value $I_{\lambda R1}$ of the target spectrum signal $S_T$ at the wavelength $\lambda_{R1}$ of the wavelength range $W_{R1}$. The wavelength $\lambda_{R1}$ may be a wavelength value in the wavelength $W_{R1}$. For example, the wavelength range $W_{R1}$ may be between 620 nm and 675 nm and the wavelength $\lambda_{R1}$ may 620 nm, 630 nm, 640 nm, 650 nm, 660 nm or 670 nm, but not limited thereto. For example, as shown in FIG. 6, the processing circuit 30 may determine whether a turning point occurs in the intensity curve of the target spectrum signal $S_T$ within the wavelength range $W_{R1}$. For example, a turning point may occur in the intensity curve of target spectrum signal $S_T$ when the intensity value of the target spectrum signal $S_T$ changes from increasing to decreasing or from decreasing to increasing. When the processing circuit 30 determines that a turning point occurs on the intensity curve of target spectrum signal $S_T$ within the wavelength range $W_{R1}$ (e.g., between 620 nm and 675 nm), the wavelength corresponding to the turning point may be chosen as the wavelength $\lambda_{R1}$. For example, as shown in FIG. 6, the wavelength $\lambda_{R1}$ may be 650 nm. Moreover, the processing circuit 30 is configured to determine an intensity value $I_{\lambda R2}$ of the target spectrum signal $S_T$ at the wavelength $\lambda_{R2}$ of the wavelength range $W_{R2}$. The wavelength $\lambda_{R2}$ may be a wavelength value in the wavelength $W_{R2}$. For example, the wavelength range $W_{R2}$ may be between 675 nm and 730 nm and the wavelength $\lambda_{R2}$ may 675 nm, 685 nm, 695 nm, 700 nm, 710 nm, 720 nm or 730 nm, but not limited thereto. For example, as shown in FIG. 6, the processing circuit 30 may determine whether a turning point occurs in the intensity curve of the target spectrum signal $S_T$ within the wavelength range $W_{R2}$. A turning point may occur in the intensity curve of target spectrum signal $S_T$ when the intensity value of the target spectrum signal $S_T$ changes from increasing to decreasing or from decreasing to increasing. When the processing circuit 30 determines that a turning point occurs on the intensity curve of target spectrum signal $S_T$ within the wavelength range $W_{R2}$ (e.g., between 675 nm and 730 nm), the wavelength corresponding to the turning point may be chosen as the wavelength $\lambda_{R1}$. For example, as shown in FIG. 6, the wavelength $\lambda_{R1}$ may be 675 nm. The tissue inflammation of the target tissue area may be calculated by dividing the intensity value $I_{\lambda R1}$ of the wavelength $\lambda_{R1}$ by the intensity value $I_{\lambda R2}$ of the wavelength $\lambda_{R2}$ (i.e. $I_{\lambda R1}/I_{\lambda R2}$) by the processing circuit 30.

In an embodiment, the health status parameter includes a tissue inflammation. The light source device 10 is configured to generate single frequency light. For example, the wavelength of the single frequency light emitted by the light source device 10 may be 522 nm, 532 nm, 600 nm, 637 nm, 673 nm, 750 nm, 785 nm or 800 nm, but not limited thereto. For example, the target tissue area to be measured is a mucosal tissue (e.g., endometrium). The light source device 10 is configured to generate the single frequency light to illuminate the target tissue area. The optical detection device 20 is configured to detect the response beams from the target tissue area to obtain a target spectrum signal $S_T$ of the target tissue area. Moreover, the processing circuit 30 is configured to calculate the tissue inflammation corresponding to the target tissue area according to the target spectrum signal $S_T$. The processing circuit 30 is configured to calculate a first intensity integration area of the target spectrum signal $S_T$ in a first wavelength range and a second intensity integration area of the target spectrum signal $S_T$ in a second wavelength range. In an embodiment, the first wavelength range is different from the second wavelength range. The first wavelength range is associated with a characteristic spectrum range of porphyrin or porphyrin derivative. The processing circuit 30 is configured to calculate the tissue inflammation corresponding to the target tissue area by dividing the first intensity integration area of the target spectrum signal $S_T$ in the first wavelength range by the second intensity integration area of the target spectrum signal $S_T$ in the second wavelength range. Therefore, the processing circuit 30 may determine the health status of the target tissue area according to the tissue inflammation corresponding to the target tissue area.

Figure 7:
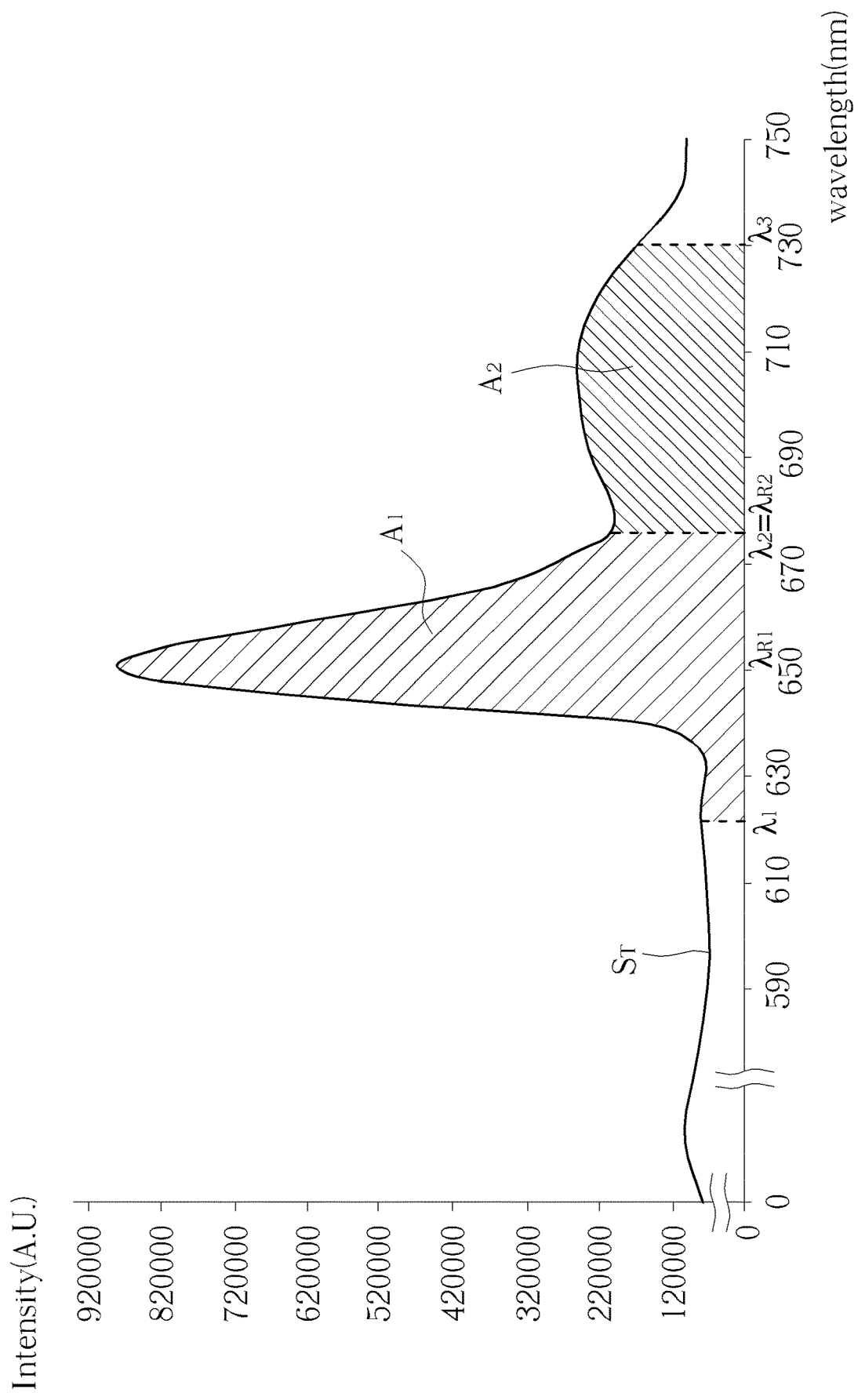

Please refer to FIG. 7, which is a schematic diagram illustrating the spectrum signals detected by the optical detection device 20 according to a fourth embodiment of the present invention. The wavelength range $W_{R1}$ is between a wavelength $\lambda_1$ and a wavelength $\lambda_2$. For example, the wavelength $\lambda_1$ is 620 nm, the wavelength $\lambda_2$ is 675 nm and the wavelength range $W_{R1}$ is between 620 nm and 675 nm. The wavelength range $W_{R2}$ is between the wavelength $\lambda_2$ and a wavelength $\lambda_3$. For example, the wavelength $\lambda_2$ is 675 nm, the wavelength $\lambda_3$ is 730 nm and the wavelength range $W_{R2}$ is between 675 nm and 730 nm. The light source device 10 is configured to generate single frequency light to illuminate the target tissue area (e.g., endometrium) and the optical detection device 20 is configured to detect a target spectrum signal $S_T$ from the target tissue area. As shown in FIG. 7, the processing circuit 30 is configured to integrate the intensity value of the target spectrum signal $S_T$ in the wavelength range $W_{R1}$ to obtain an intensity integration area $A_1$ of the target spectrum signal $S_T$ in the wavelength range $W_{R1}$. The intensity integration area $A_1$ may be the area under the curve of the target spectrum signal $S_T$ between the wavelength $\lambda 1$ and the wavelength $\lambda_2$. The processing circuit 30 is configured to integrate the intensity value of the target spectrum signal $S_T$ in the wavelength range $W_{R2}$ to obtain an intensity integration area $A_2$ of the target spectrum signal $S_T$ in the wavelength range $W_{R2}$. The intensity integration area $A_2$ may be the area under the curve of the target spectrum signal $S_T$ between the wavelength $\lambda_2$ and the wavelength $\lambda_3$. The processing circuit 30 is configured to calculate the tissue inflammation corresponding to the target tissue area by dividing the intensity integration area $A_1$ by the intensity integration area $A_2$ (i.e. $A_1/A_2$).

In an embodiment, the health status parameter includes a tissue uniformity. The light source device 10 is configured to generate single frequency light. For example, the wavelength of the single frequency light emitted by the light source device 10 may be 522 nm, 532 nm, 600 nm, 637 nm, 673 nm, 750 nm, 785 nm or 800 nm, but not limited thereto. For example, the target tissue area to be measured is a mucosal tissue (e.g., endometrium). The reference tissue area is a healthy tissue of the same human body as the target tissue area. For example, the reference tissue area may be a healthy oral mucosa. The target tissue area may include a plurality of sub-target tissue areas. The optical detection device 10 is configured to generate the single frequency light to illuminate the plurality of sub-target tissue areas of the target tissue area. The optical detection device 20 is configured to detect a plurality of sub-target spectrum signal from the plurality of sub-target tissue areas of the target tissue area. Each sub-target spectrum signal corresponds to a respective sub-target tissue area. The processing circuit 30 is configured to calculate the tissue uniformity according to the plurality of sub-target spectrum signals of the plurality of sub-target tissue areas. For example, as the target tissue area includes sub-target tissue areas $S_{A1}$ to $S_{An}$, the optical detection device 20 detects a respective sub-target spectrum signal for each sub-target tissue area. For example, the optical detection device 20 detects a sub-target spectrum signal $S_{T1}$ of the sub-target tissue area $S_{A1}$, a sub-target spectrum signal $S_{T2}$ of the sub-target tissue area $S_{A2}$, and such like this, the optical detection device 20 detects sub-target spectrum signals $S_{T1}$ to $S_{Tn}$ of the sub-target tissue areas $S_{A1}$ to $S_{An}$.

The processing circuit 30 may calculate a sub-target intensity area of the sub-target spectrum signal in a first wavelength range for each sub-target tissue area. The first wavelength range may be between 300 nm and 380 nm, 400 nm and 600 nm, 500 nm and 650 nm, 600 nm and 850 nm, 640 nm and 800 nm, 400 nm and 900 nm or 600 nm and 1050 nm, but not limited thereto. For example, the processing circuit 30 calculates a sub-target intensity area $A_1$ of the sub-target spectrum signal $S_{T1}$ in the first wavelength range, a sub-target intensity area $A_2$ of the sub-target spectrum signal $S_{T2}$ in the first wavelength range, a sub-target intensity area $A_3$ of the sub-target spectrum signal $S_{T13}$ in the first wavelength range, and such like this, the processing circuit 30 calculates sub-target tissue areas $S_{A1}$ to $S_{An}$ of the sub-target spectrum signals $S_{T1}$ to $S_{An}$ in the first wavelength range. The processing circuit 30 may calculate a sum of absolute differences between each pair of the sub-target tissue areas $S_{A1}$ to $S_{An}$ of the sub-target spectrum signals $S_{T1}$ to $S_{An}$ in the first wavelength range to obtain a calculation result and calculate the tissue uniformity of the target tissue area by dividing a maximum value of the sub-target tissue areas $S_{A1}$ to $S_{An}$ by the calculation result of the sum of absolute difference operation. The tissue uniformity of the target tissue area may be calculated by the processing circuit 30 according to the following equation:

$$U = \frac{\max\{A_k, k = 1, \ldots, n\}}{\sum_{i=1}^{n-1}\sum_{j=i+1}^{n} |A_i - A_j|}, A_1, \ldots, A_n \quad (4)$$

where U represents the tissue uniformity, $A_1$ to $A_n$ represent intensity integration areas of the sub-target spectrum signals $S_{T1}$ to $S_{Tn}$ in the first wavelength range, Max( ) represents a function indicating taking a maximum of the value in the following parentheses; |·| represents an absolute value operation; and i, j, k, n are positive integers.

Figure 8:
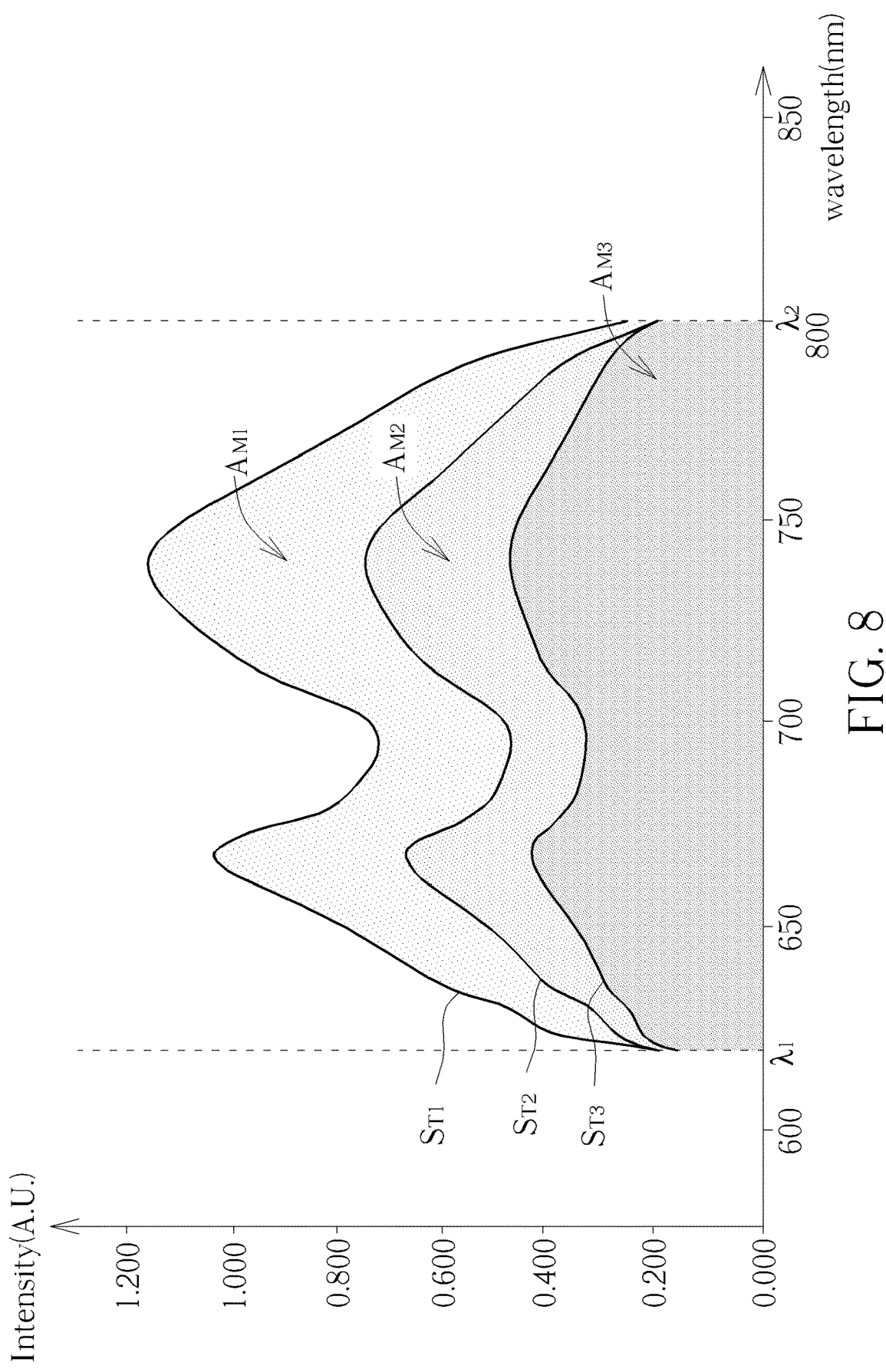

Please refer to FIG. 8, which is a schematic diagram illustrating the spectrum signals detected by the optical detection device 20 according to a fifth embodiment of the present invention. The wavelength range $W_{R1}$ may be between 640 nm and 800 nm. The light source device 10 is configured to generate single frequency light (e.g., with wavelength of 600 nm) to illuminate sub-target tissue areas $S_{A1}$ to $S_{A3}$ of the target tissue area (e.g., endometrium). The optical detection device 20 is configured to detect a sub-target spectrum signal $S_{T1}$ from the sub-target tissue area $S_{A1}$, a sub-target spectrum signal $S_{T2}$ from the sub-target tissue area $S_{A2}$ and a sub-target spectrum signal $S_{T3}$ from the sub-target tissue area $S_{A3}$. As shown in FIG. 8, the processing circuit 30 is configured to integrate the intensity value of the sub-target spectrum signal $S_{T1}$ in the wavelength range $W_{R1}$ to obtain an intensity integration area $A_{M1}$ of the sub-target spectrum signal $S_{T1}$ in the wavelength range $W_{R1}$. The intensity integration area $A_{M1}$ may be the area under the curve of the sub-target spectrum signal $S_{T1}$ between 640 nm and 800 nm. Similarly, the processing circuit 30 is configured to integrate the intensity value of the sub-target spectrum signal $S_{T2}$ in the wavelength range $W_{R1}$ to obtain an intensity integration area $A_{M2}$ of the sub-target spectrum signal $S_{T2}$ in the wavelength range $W_{R1}$ and integrate the intensity value of the sub-target spectrum signal $S_{T3}$ in the wavelength range $W_{R1}$ to obtain an intensity integration area $\lambda_{M3}$ of the sub-target spectrum signal $S_{T2}$ in the wavelength range $W_{R1}$. The equation (5) may be obtained by substituting the intensity integration areas $A_{M1}$ to $A_{M3}$ into the equation (4) by the processing circuit 30. Therefore, the tissue uniformity of the target tissue area may be calculated by the processing circuit 30 according to the following equation:

$$U = \frac{\max\{AM1, AM2, AM3\}}{|AM1 - AM2| + |AM2 - AM3| + |AM1 - AM3|} \quad (5)$$

where U represents the tissue uniformity, $\lambda_{M1}$, $\lambda_{M2}$, $\lambda_{M3}$ represent intensity integration areas of the sub-target spectrum signals $S_{T1}$, $S_{T2}$, $S_{T3}$ in the wavelength range $W_{R1}$, respectively, Max( ) represents a function indicating taking a maximum of the value in the following parentheses, and |·| represents an absolute value operation.

As the tissue uniformity of the target tissue area is calculated, the processing circuit 30 may evaluate and determine the health status of the target tissue area according to the calculated tissue uniformity of the target tissue area. For example, as the calculated tissue uniformity of the target tissue area does not fall within the normal range of healthy mucosal tissue, this means there is significant difference among the spectrum signals of different measured areas due to the uneven endometrial tissue structure, and thus the person to be measured is hard to get pregnant at this time and is currently not in the WOI period.

Those skilled in the art should readily make combinations, modifications and/or alterations on the abovementioned description and examples. The abovementioned description, steps, procedures and/or processes including suggested steps can be realized by means that could be hardware, software, firmware (known as a combination of a hardware device and computer instructions and data that reside as read-only software on the hardware device), an electronic system or combination thereof. An example of the means may be the optical measurement system 1. Examples of hardware can include analog, digital and/or mixed circuits known as microcircuit, microchip, or silicon chip. For example, the hardware may include ASIC(s), field programmable gate array(s) (FPGA(s)), programmable logic device (s), coupled hardware components or combination thereof. In another example, the hardware may include general-purpose processor(s), microprocessor(s), controller(s), digital signal processor(s) (DSP (s)) or combination thereof. Examples of the software may include set(s) of codes, set(s) of instructions and/or set(s) of functions retained (e.g., stored) in a storage device, e.g., a non-transitory computer-readable medium. The non-transitory computer-readable storage medium may include read-only memory (ROM), flash memory, random access memory (RAM), subscriber identity module (SIM), hard disk, floppy diskette, or CD-ROM/DVD-ROM/BD-ROM, but not limited thereto. Any of the abovementioned procedures and examples above may be compiled into program codes or instructions that are stored in a non-transitory storage device or a computer-readable medium. The processing circuit 30 may read and execute the program codes or the instructions stored in the storage device storage device or computer-readable medium for realizing the abovementioned functions.

In summary, the embodiments of the present invention may calculate health status parameters according to the target spectrum signal corresponding to the target tissue area and the reference spectrum signal corresponding to the reference tissue area for real time measurement. Compared with the conventional endoscope method, the optical inspection system of the embodiments of the present invention may significantly reduce the discomfort and pain for the person to be measured during the measurement process. Furthermore, the conventional optical laser diagnosis method is typically performed based on the image information of the mucosal surface for diagnosis. In comparison, the detection result of the embodiments of the present invention may be quantifiable values rather than the images that cannot be quantified, thus reducing the probability of human errors caused by naked eye judgment. The embodiments of the present invention may also provide real-time health parameters which are calculated and determined by utilizing spectrum signals and accurately utilized as reference values for early mucosal symptoms, thus significantly improving diagnostic accuracy.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An optical measurement system, comprising:
   a light source device configured to generate light to illuminate a target tissue area and a reference tissue area of a human body;
   a fiber module coupled to the light source device, and configured to direct and transmit the light generated by the light source device to illuminate the target tissue area and the reference tissue area of the human body, and receive response beams from the target tissue area and the reference tissue area of the human body;
   an optical detection device coupled to the fiber module, and configured to detect the response beams from the target tissue area to obtain a target spectrum signal of the target tissue area and detect the response beams from the reference tissue area to obtain a reference spectrum signal of the reference tissue area; and
   a processing circuit coupled to the light source device and optical detection device, and configured to calculate a health status parameter of the target tissue area according to the target spectrum signal and the reference spectrum signal;
   wherein the health status parameter comprises a tissue oxygenation, the processing circuit is configured to determine at least one reference peak intensity value of the reference spectrum signal in a first wavelength range, determine a reference intensity value of the reference spectrum signal at a first characteristic wavelength, and accordingly calculate a reference absorption intensity value of the reference spectrum signal at the first characteristic wavelength, the processing circuit is configured to determine at least one peak intensity value of the target spectrum signal in the first wavelength range, determine a target intensity value of the target spectrum signal at the first characteristic wavelength, and accordingly calculate a target absorption intensity value of the target spectrum signal at the first characteristic wavelength, and the processing circuit is configured to calculate the tissue oxygenation of the target tissue area according to the reference absorption intensity value and the target absorption intensity value.

2. The optical measurement system of claim 1, wherein the light source device comprises a single frequency light source having a wavelength of 280 nm, 365 nm, 405 nm, 522 nm, 465 nm, 532 nm, 600 nm, 637 nm, 750 nm, 785 nm, 800 nm or 1064 nm.

3. The optical measurement system of claim 2, wherein the single frequency light source comprises a laser diode.

4. The optical measurement system of claim 1, wherein the light source device comprises a broadband light source in a wavelength range of 200 nm to 500 nm, 400 nm to 600 nm, 500 nm to 650 nm, 400 nm to 900 nm or 600 nm to 1050 nm.

5. The optical measurement system of claim 4, wherein the broadband light source comprises a light emitting diode.

6. The optical measurement system of claim 1, wherein the target tissue area is a mucosal tissue.

7. The optical measurement system of claim 6, wherein the target tissue area is an endometrium.

8. The optical measurement system of claim 7, wherein the target tissue area is the endometrium located at the fundus of a uterus, the cavity of uterus, the entrance of uterus adjacent to a cervix, the internal of a cervix or the external of a cervix.

9. The optical measurement system of claim 1, wherein the reference tissue area is a healthy tissue of the same human body as the target tissue area.

10. The optical measurement system of claim 9, wherein the reference tissue area is a tissue of a pad of a finger or a tissue of an inner side of a thigh.

11. The optical measurement system of claim 1, wherein the processing circuit is configured to calculate an average value of the at least one reference peak intensity value, calculate the reference absorption intensity value of the reference spectrum signal at the first characteristic wavelength by subtracting the reference intensity value of the reference signal at the first characteristic wavelength from the average value of the at least one reference peak intensity value, calculate an average value of the at least one target peak intensity value, calculate the target absorption intensity value of the target spectrum signal at the first characteristic wavelength by subtracting the target intensity value of the target signal at the first characteristic wavelength from the average value of the at least one target peak intensity value, and the processing circuit is configured to calculate the tissue oxygenation of the target tissue area by dividing the target absorption intensity value of the target spectrum signal at the first characteristic wavelength by the reference absorption intensity value of the reference spectrum signal at the first characteristic wavelength.

12. The optical measurement system of claim 1, wherein the first characteristic wavelength is in the first wavelength range, the first wavelength range is between 500 nm and 650 nm or 650 nm and 950 nm, the first characteristic wavelength is 568 nm, 578 nm, 588 nm, 650 nm, 660 nm or 670 nm, or the first characteristic wavelength is between 568 nm and 588 nm or 650 nm and 670 nm.

13. The optical measurement system of claim 1, wherein the first characteristic wavelength is associated with a characteristic wavelength of oxygenated hemoglobin.

* * * * *